United States Patent [19]

Fairhurst et al.

[11] Patent Number: 5,389,684

[45] Date of Patent: Feb. 14, 1995

[54] NAPHTHALENE CARBOXAMIDES

[75] Inventors: John Fairhurst, Basingstoke; David E. Tupper, Reading, both of United Kingdom

[73] Assignee: Lilly Industries Limited, Basingstoke, United Kingdom

[21] Appl. No.: 108,038

[22] Filed: Aug. 17, 1993

[30] Foreign Application Priority Data

Aug. 26, 1992 [GB] United Kingdom ............... 9218113

[51] Int. Cl.[6] ................... A61K 31/165; C07C 233/22
[52] U.S. Cl. ..................... 514/622; 514/618; 514/619; 564/162; 564/166; 564/172
[58] Field of Search ............... 564/170, 171, 172, 173, 564/162, 166; 514/622, 618, 619

[56] References Cited

U.S. PATENT DOCUMENTS

| | | | |
|---|---|---|---|
| 2,766,173 | 10/1956 | Ziegler | 167/52 |
| 3,662,070 | 5/1972 | Thominet | 424/274 |
| 3,829,467 | 8/1974 | Diamond | 260/501.16 |
| 3,838,169 | 9/1974 | Thominet | 260/330.5 |
| 4,059,621 | 11/1977 | Vincent et al. | 260/558 R |
| 4,540,814 | 9/1985 | Carter, Jr. | 564/172 |
| 4,649,139 | 3/1987 | Allan et al. | 514/242 |
| 4,782,080 | 11/1988 | Witzel | 814/443 |
| 5,096,908 | 3/1992 | Gidda et al. | 514/233.5 |
| 5,118,680 | 6/1992 | Muller et al. | 514/307 |

FOREIGN PATENT DOCUMENTS

| | | |
|---|---|---|
| 160408 | 1/1985 | European Pat. Off. . |
| 1234699 | 7/1968 | United Kingdom . |
| 2193961A | 2/1988 | United Kingdom . |

OTHER PUBLICATIONS

Monkovic, "New Benzamide Anti-Emetics", *Drugs of the Future*, 14:1, 41–49 (1989).

Gonzalez-Heydrich et al., *J. Clin. Psychiatry*, 51, 4 (1990).
Fuller et al., *Advances in Drug Research*, 17, 349 (1988).
Dreteler et al., *J. Card. Pharm.*, 14, 770 (1989).
Shepheard et al., *Eur. J. Pharm.*, 186, 267 (1990).
Lucot et al., *Pharm. Biochem. & Beh.*, 33, 627 (1989).
Othmer et al., *J. Clin. Psych.*, 48(5), 201 (1987).
European Search Report (Feb. 19, 1993) EP 92 31 0406.
Banitt et al; J. Med. Chem. 18(1130–34) 1975.

*Primary Examiner*—Glennon H. Hollrah
*Assistant Examiner*—Brian M. Burn
*Attorney, Agent, or Firm*—MaCharri Vorndran-Jones

[57] ABSTRACT

Pharmaceutical compounds of the formula:

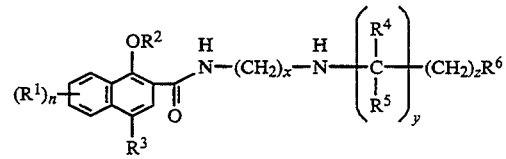

in which each $R^1$ is hydrogen, $C_{1-4}$ alkyl, $C_{1-4}$ alkoxy, halogen or nitro, and n is 0, 1, 2 or 3, $R^2$ is hydrogen, $C_{1-4}$ alkyl or $C_{2-4}$ alkenyl, $R^3$ is hydrogen, $C_{1-4}$ alkyl, $C_{1-4}$ alkoxy, $C_{1-4}$ alkylthio, halogen, nitro or —NR'R" where R' and R" are each hydrogen or $C_{1-4}$ alkyl, $R^4$ and $R^5$ are each hydrogen, $C_{1-4}$ alkyl, optionally substituted phenyl or $C_{6-9}$ cycloalkyl optionally substituted by 1 to 4 $C_{1-4}$ alkyl groups, $R^6$ is optionally substituted phenyl, tetrahydronaphthyl, phthalimido, sacchariny, glutaramido, $C_{6-10}$ cycloalkyl optionally substituted with 1 to 4 $C_{1-4}$ alkyl groups or a phenyl group, or $C_{4-9}$ heterosubstituted cycloalkyl optionally substituted with 1–4 alkyl groups, x is 1, 2 or 3, y is 0 or 1 and z is 0, 1, 2 or 3; and salts thereof.

7 Claims, No Drawings

NAPHTHALENE CARBOXAMIDES

This invention relates to novel compounds and their use as pharmaceuticals.

The compounds of the invention are of the formula (I):

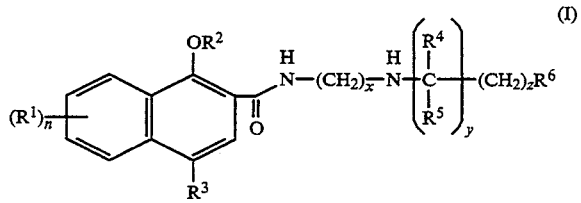

in which each $R^1$ is hydrogen, $C_{1-4}$ alkyl, $C_{1-4}$ alkoxy, halogen or nitro, and n is 0, 1, 2 or 3, $R^2$ is hydrogen, $C_{1-4}$ alkyl or $C_{2-4}$ alkenyl, $R^3$ is hydrogen, $C_{1-4}$ alkyl, $C_{1-4}$ alkoxy, $C_{1-4}$ alkylthio, halogen, nitro or $-NR'R''$ where $R'$ and $R''$ are each hydrogen or $C_{1-4}$ alkyl, $R^4$ and $R^5$ are each hydrogen, $C_{1-4}$ alkyl, optionally substituted phenyl or $C_{6-9}$ cycloalkyl optionally substituted by 1 to 4 $C_{1-4}$ alkyl groups, $R^6$ is optionally substituted phenyl, tetrahydronaphthyl, phthalimido, saccharinyl, glutaramido, $C_{6-10}$ cycloalkyl optionally substituted with 1 to 4 $C_{1-4}$ alkyl groups or a phenyl group, or $C_{4-9}$ heterosubstituted cycloalkyl optionally substituted with 1-4 alkyl groups, x is 1, 2 or 3, y is 0 or 1 and z is 0, 1, 2 or 3; and salts thereof.

Compounds of formula (I) have been found to possess useful biological properties, and in particular they are indicated for use in the treatment of disorders of the central nervous system.

In the above formula (I), a $C_{1-4}$ alkyl group is, for example, a methyl, ethyl, propyl, isopropyl, butyl or t.butyl group, and is preferably methyl or ethyl. A $C_{1-4}$ alkoxy group is one such alkyl group linked through oxygen to the phenyl nucleus. A halogen group is, preferably chloro, bromo or fluoro. A $C_{2-4}$ alkenyl group is preferably of the formula $-(CH_2)_nCH=CH_2$ where n is 0, 1 or 2, and a preferred example is allyl. It is preferred that a phenyl group is unsubstituted, but it can be substituted with one or more, preferably 1 to 3, substituents selected, for example, from halogen, $C_{1-4}$ alkyl, $C_{1-4}$ alkoxyl, hydroxy, nitro, cyano, amino, carboxy and carboxamido. Preferably a substituted phenyl nucleus has one or two substituents selected from halogen, $C_{1-4}$ alkyl, especially methyl or ethyl, and $C_{1-4}$ alkoxy, especially methoxy or ethoxy.

When n is 2 or 3 the substituent groups can be the same or different, but n is preferably 0. It is preferred that $R^2$ is $C_{1-4}$ alkyl, and especially preferred values of $R^1$ and $R^2$ are hydrogen and methyl, respectively. $R^3$ is preferably $C_{1-4}$ alkoxy, $C_{1-4}$ alkylthio, halogen, nitro $-NH_2$ or $-N(CH_3)_2$.

When $R^4$, $R^5$ or $R^6$ is $C_{6-9}$ cycloalkyl, it can be, for example, cyclohexyl, cycloheptyl, cyclooctyl, a bridged group such as for example, bicyclooctyl, norbornyl or adamantyl. Preferred values are cyclohexyl, cycloheptyl and cyclooctyl. $R^6$ can in addition be a $C_{10}$-cycloalkyl group such as for example adamantyl. When $R^4$, $R^5$ or $R^6$ is a heterosubstituted cycloalkyl group one or more carbon atoms of the cycloalkyl group is replaced by a heteroatom, and examples include tetrahydropyranyl, tetrahydrothiopyranyl, morpholino, piperidino and piperazinyl, the group being attached via a hetero atom or by one of the carbon atoms of the cyclo nucleus. Preferably the group contains 4 or 5 carbon atoms.

Cycloalkyl groups can be substituted by 1 to 4 $C_{1-4}$ alkyl, especially methyl, groups, but are preferably unsubstituted.

With regard to the values of x, y and z, x is preferably 2, and y and z are preferably 0.

Preferred terminal amino groups are of the formula:

$$-NH-(CH_2)_zR^6 \qquad (1)$$

where z is 0, 1 or 2, especially 0, and $R^6$ is $C_{6-9}$ cycloalkyl, or $$-NH-CHR^5R^6 \qquad (2)$$

where $R^5$ and $R^6$ are each $C_{6-9}$ cycloalkyl.

A preferred group of compounds of formula (I) above, is one in which $R^1$ is hydrogen, $R^2$ is $C_{1-4}$ alkyl, especially methyl, $R^6$ is $C_{6-9}$ cycloalkyl, x is 2, and either (1) y is 0 and z is 0, 1 or 2, or (2) $R^4$ is hydrogen, $R^5$ is $C_{6-9}$ cycloalkyl, y is 1 and z is 0.

The compounds of the invention are useful both in their free base and acid addition salt forms. The acid addition salts are preferably the pharmaceutically acceptable, non-toxic additional salts with suitable acids, such as those with inorganic acids, for example hydrochloric, hydrobromic, nitric, sulphuric or phosphoric acids, or with organic acids, such as organic carboxylic acids, for example, oxalic, glycollic, maleic, hydroxymaleic, fumaric, malic, tartaric, citric or lactic acid, or organic sulphonic acids for example methane sulphonic, ethane sulphonic, 2-hydroxyethane sulphonic, toluene-p-sulphonic or naphthalene-2-sulphonic acid. Apart from pharmaceutically acceptable acid addition salts, other salts are also included within the scope of acid addition salts such as, for example, those with picric or oxalic acid, since they may serve as intermediates in the purification of the compounds or in the preparation of other, for example, pharmaceutically acceptable, acid addition salts, or are useful for identification, characterization or purification of the bases.

The invention also includes a process for producing a compound according to formula (I) above, which comprises (a) reacting a compound of the formula:

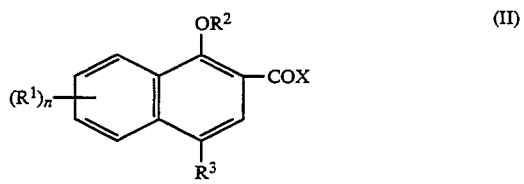

where X is a leaving group, with a compound of the formula:

$$H_2N(CH_2)_xNH(CR^4R^5)_y(CH_2)_zR^6 \qquad (III)$$

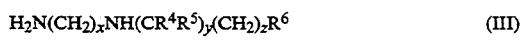

(b) alkylating a compound of the formula:

(c) reacting a compound of the formula:

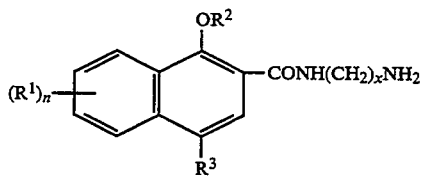

where Y is a leaving group, with a compound of the formula:

H₂N (CR⁴R⁵)ᵧ(CH₂)ᵤR⁶; or (d) alkylating a compound of the formula:

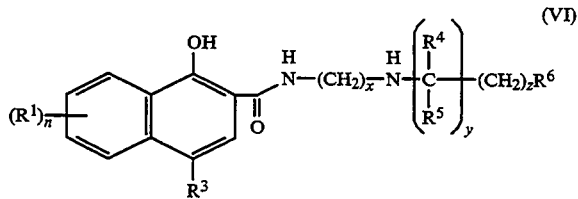

With regard to process variant (a), the reaction is preferably carried out in an organic solvent such as for example dichloromethane, chloroform, dimethylformamide or acetonitrile, and preferably at a temperature of from 0° C. to 150° C., such as at room temperature.

The intermediate of formula (II) can be prepared in situ and the leaving group X can be any of those commonly employed, such as for example imidazolide, halide and $C_{1-4}$ alkane sulphonate. The compounds are derived from known 1-hydroxy-2-naphthoic acids, which are optionally alkylated at the 1-position, and reacted with a suitable reagent, such as for example carbonyl diimidazole to provide the compound of formula (II).

The amine reactants of formula (III) can be prepared from the appropriate alkylene diamine of formula H₂N(CH₂)ₓNH₂ by reaction with aldehyde or ketone to provide a Schiff's base which can be reduced, catalytically, by for example, palladium or charcoal or, chemically, employing for example, sodium borohydride, to give the described amine.

With regard to process variant (b), the reaction is preferably performed in an organic solvent such as for example dichloromethane or dimethylformamide, and preferably at a temperature of from 0° C. to 150° C., such as at room temperature.

The amine reactant of formula (IV) can be prepared by reacting a compound of formula (II) with the appropriate alkylene diamine, and alkylation can be accomplished (1) by the action of the appropriate alkylating agent of formula:

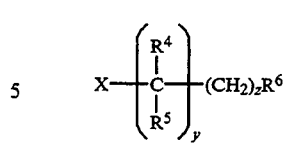

where x is, for example, halogen, or (2) by reaction with the appropriate aldehyde or ketone, followed by reduction.

With regard to process variant (c), the reaction is preferably carried out in an organic solvent such as for example dimethylformamide, dichloromethane or acetonitrile, and preferably at a temperature of from 0° C. to 150° C., for example at room temperature. The reactant of formula (V) can be prepared by reacting a compound of formula (II) with the appropriate amine of formula H₂N(CH₂)ₓY, Y being a leaving group such as for example, halogen, especially bromo, or chloro.

With regard to process variant (d), the reaction can be carried out in an organic solvent, such as for example DMF, in the presence of a base such as sodium hydride or potassium t-butoxide, and preferably at a temperature of from 20° C. to 100° C. An alkylating agent of the formula R²X where X is for example Cl or Br is employed. The starting compound of formula (VI) can readily be prepared by one or other of the routes defined in process variants (a) to (c), or by dealkylation of a compound of formula (I).

As mentioned above, the compounds of the invention have useful central nervous system activity. The compounds have high affinity for the serotonin 5-HT$_{1A}$ receptor. Their binding activity has been demonstrated in the test described by Wong et al, *J. Neural Transm.*, 71, 207 (1988) in which binding to the serotonin-1A receptor is measured in competition with ³H-8-hydroxy-2-(di-n-propylamino)-tetralin, and the compounds of the invention described in the following Examples have an IC 50 in the test of less than 100 nm.

Because of their selective affinity for the 5-HT$_{1A}$ receptor, the compounds of the present invention are indicated for use in treating a variety of conditions such as obesity, bulemia, depression, hypertension, aging, memory loss, sexual dysfunction, anxiety, schizophrenia, gastrointestinal disorders, headaches and cardiovascular disorders.

The compounds of the invention are effective over a wide dosage range, the actual dose administered being dependent on such factors as the particular compound being used, the condition being treated and the type and size of mammal being treated. However, the dosage required will normally fall within the range of 0.01 to 20 mg/kg per day, for example in the treatment of adult humans, dosages of from 0.5 to 100 mg per day may be used.

The compounds of the invention will normally be administered orally or by injection and, for this purpose, the compounds will usually be utilised in the form of a pharmaceutical composition. Such compositions are prepared in a manner well known in the pharmaceutical art and comprise at least one active compound.

Accordingly the invention includes a pharmaceutical composition comprising as active ingredient a compound of formula (I) or a pharmaceutically acceptable salt thereof, associated with a pharmaceutically acceptable carrier. In making the compositions of the invention, the active ingredient will usually be mixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for active ingredient. Some examples of suitable carriers are lactose, dextrose, sucrose, sorbitol, mannitol, starches, gum acacia, calcium phosphate, alginates, tragacanth, gelatin, syrup, methyl cellulose, methyl- and propylhydroxybenzoate, talc, magnesium stearate or mineral oil. The compositions of the invention may, if desired, be formulated so as to provide quick, sustained or delayed release of the active ingredient after administration to the patient.

Depending on the route of administration, the foregoing compositions may be formulated as tablets, capsules or suspensions for oral use and injection solutions for parenteral use or as suppositories. A preferred formulation is an injection especially a sustained release formulation for intra-muscular injection. Preferably the compositions are formulated in a dosage unit form, each dosage containing from 0.5 to 100 mg, more usually 1 to 100 mg, of the active ingredient.

The following Preparations and Examples illustrate the invention:

Preparation 1

4-Bromo-1-hydroxy naphthalene-2-carboxylic acid

To a suspension of 1-hydroxy-2-naphthoic acid (2.5 g; 13.3 mm) in chloroform (50 ml) was added bromine (0.68 ml) in chloroform (5 ml) dropwise and the reaction stirred at room temperature for one hour. The solvent was removed in vacuo, the solid washed repeatedly with water and collected by filtration and dried to give 4-bromo-1-hydroxy-naphthalene-2-carboxylic acid as a white solid.

Preparation 2

4-Chloro-1-hydroxy-naphthalene-2-carboxylic acid

To a suspension of 1-hydroxy-2-naphthoic acid (3.76 g; 0.02 m) in chloroform (50 ml) was added sulphuryl chloride (2.97 g; 0.022 m) dropwise and the solution stirred at room temperature for two hours. The solvent was removed in vacuo to give a white solid which was washed with water, collected and dried. The crude solid was recrystallised from ethanol to give 4-chloro-1-hydroxy-naphthalene-2-carboxylic acid as white needles.

Preparation 3

1-Hydroxy-5-methoxy-naphthalene-2-carboxylic acid

5-Methoxy-1-naphthol (17.4 g; 0.1 m) was dissolved in THF (200 ml) and sodium hydride (5.28 g of 50% dispersion in oil; 0.11 m) was added portionwise. Following this addition, the solution was warmed to 50° C. to ensure complete anion formation and then cooled to room temperature. Diethyl carbamoyl chloride (14.9 g; 14 ml; 0.11 m) was added slowly, keeping the resultant exotherm to <40° C., and then the solution left overnight at room temperature. THF was removed in vacuo and ethyl acetate (200 ml) with water (200 ml) added. After separation of the organics and two further extractions with ethyl acetate (2×100 ml), the organics were collected, washed with water (2×100 ml), dried over anhydrous magnesium sulphate, filtered and the solvent removed in vacuo to give a dark viscous oil. After flash chromatography eluting with dichloromethane, O-5-methoxy naphthyl diethyl carbamate (19.8 g) solidified on cooling.

O-5-Methoxy naphthyl diethyl carbamate (2.45 g; 0.01 m) was dissolved in dry THF (20 ml) containing TMEDA (1.66 ml; 0.011 m) and sec-BuLi (8.5 ml; 1.3M solution; 0.01 m) was added dropwise to this solution cooled to -78° C. under a stream of nitrogen. After one hour, dry $CO_2$ was passed through the reaction mixture for two hours and the solution allowed to warm to room temperature overnight. The reaction mixture was treated with saturated ammonium chloride (15 ml) and the whole solution evaporated to dryness. The residue was extracted with ether (3×50 ml) and the aqueous layer acidified with 2N HCl. The acidified aqueous layer was extracted with ethyl acetate (3×30 ml), the organics collected and washed with water (3×50 ml), dried over anhydrous magnesium sulphate, filtered and the solvent removed in vacuo to give 2.5 g of O-2-carboxy-5-methoxy naphthyl diethyl carbamate.

This product (2.4 g) was dissolved in ethanol (20 ml) containing 2N sodium hydroxide (16 ml) and the solution refluxed for two hours. After cooling and adding 5N hydrochloric acid, the product was extracted with ethyl acetate (3×50 ml) and the organics collected and washed with saturated brine solution (2×30 ml). The organics were collected, dried over anhydrous magnesium sulphate, filtered and vacued to a solid, 1-hydroxy-5-methoxy-naphthalene-2-carboxylic acid.

Preparation 4

4-Bromo-1-methoxy-naphthalene-2-carboxylic acid

4-Bromo-1-hydroxy-naphthalene-2-carboxylic acid (3.2 g; 0.012 m) was dissolved in acetone (50 ml) and anhydrous potassium carbonate (4.97 g; 0.036 m) and dimethyl sulphate (3.4 ml; 0,036 m) added. The solution was refluxed for one hour, cooled and then the solvent removed in vacuo. This was dissolved in ethyl acetate (50 ml) and water (50 ml) added. Two further extractions with ethyl acetate (2×50 ml), washing the collected organics with water (2×50 ml), drying over magnesium sulphate and filtering gave, after removal of the solvent, methyl 4-bromo-1-methoxy-naphthalene-2-carboxylate as crude product.

This product (3.5 g) was dissolved in ethanol (40 ml) and 2N sodium hydroxide (10 ml) added. The solution was refluxed for four hours, then added to ice-water and acidified with 5N hydrochloric acid. The thick white precipitate was filtered, washed to neutrality with water and dried to give 4-bromo-1-methoxy-naphthalene-2-carboxylic acid.

Similarly prepared were:
1-methoxy naphthalene-2-carboxylic acid
1,4-dimethoxy naphthalene-2-carboxylic acid
1,5-dimethoxy naphthalene-2-carboxylic acid
4-chloro-1-methoxy-naphthalene-2-carboxylic acid Preparation 5

1-Methoxy-4-methylthio naphthalene-2-carboxylic acid

To a suspension of 4-bromo-1-methoxy-naphthalene 2-carboxylic acid (28 g; 0.1 m) in dichloromethane (100 ml) was added oxalyl chloride in one portion (at 0° C.) followed by dry dimethyl formamide (1.5 ml). After some vigorous effervescence, the solution was stirred at room temperature for two hours. This solution was then taken to dryness in vacuo, the solid dissolved in dichloromethane (100 ml) and added dropwise to a stirred solution of 2-amino-2-methyl propan-1-ol (17.8 g; 0.2 m)

in dichloromethane (100 ml). This solution was stirred at room temperature for three hours and after filtration the solvent was removed in vacuo to give a golden oil (31 g).

This was dissolved in carbon tetrachloride (150 ml) and thionyl chloride (21.9 ml; 0.3 m) added dropwise, a precipitate forming gradually. A further volume of carbon tetrachloride (100 ml) was added and the solution left stirring for 30 minutes. The precipitate was filtered, neutralised with 2N sodium hydroxide and extracted with ether (3×150 ml). After drying the collected organics over anhydrous magnesium sulphate, filtering and removal of the solvent under vacuum, a golden oil was produced (28 g), namely 4-bromo-2-(1-methoxy naphthyl)-4,4-dimethyl-2-oxazoline.

To this product (7.5 g; 0.0225 m) in dry tetrahydrofuran (150 ml) was added n-BuLi (155 ml; 0.0248 n; 1.6M solution) at −78° C. under nitrogen. After stirring for one hour at this temperature, dimethyl disulphide (6.36 ml; 0.07 m) was added, with the temperature rising to −50° C. After four hours, water (100 ml) was added and the product extracted with dichloromethane (3×100 ml). After drying, filtering and removal of solvent in vacuo, a golden oil was produced (4.8 g). This oil (1.8 g) was dissolved in 5N hydrochloric acid (100 ml) and refluxed for eight hours. After cooling, the precipitate was dissolved in ethyl acetate (50 ml). Two further extractions ethyl acetate (2×50 ml), washing with brine (2×50 ml), drying, filtering and removal of solvent in vacuo gave a yellowish solid (1.2 g). Flash chromatography eluding with 2% methanol/dichloromethane gave a solid, which was recrystallised from ethyl acetate (1.0 g), namely 1-methoxy-4-methylthio naphthalene 2-carboxylic acid.

Preparation 6

1,3-Dimethoxy-naphthalene-2-carboxylic acid

Ethyl-1,3-dihydroxy naphthalene-2-carboxylic acid (Org. Synth. III, 637) (11.6 g; 0.05 m), potassium carbonate (13.8 g, 0.1 m) and dimethyl sulphate (12.6 g; 0.1 m) in acetone (150 ml) were heated at reflux for 18 hours. The reaction mixture was poured into ice water and the product separated by filtration, washed with water and dried to give ethyl-1,3-dimethoxy naphthalene-2-carboxylate.

This material was suspended in 2N NaOH (100 ml) and heated at reflux for 18 hours. The reaction was poured into ice water and made acid with 5N HCl. The product was collected by filtration, washed with water and dried to give 1,3-dimethoxy-naphthalene-2-carboxylic acid.

Preparation 7

1-Methoxy-4-nitro naphthalene-2-carboxylic acid

To a stirred solution of 1-methoxy-naphthalene-2-carboxylic acid (20.2 g; 0.1 m) in glacial acetic acid (200 ml) was added a solution of potassium nitrate (10.1 g; 0.1 m) in concentrated sulphuric acid (10 ml). The temperature was maintained below 25° C. by means of a water bath. The reaction was stirred for four hours and poured into ice-water (500 ml). The product was collected by filtration, washed well with water and dried in vacuo at room temperature to give 1-methoxy-4-nitro naphthalene-2-carboxylic acid, m.p. 204°–206° C.

Methyl-1-methoxy-4-nitro-naphthalene-2-carboxylate was similarly prepared from methyl-1-methoxy naphthalene-2-carboxylate, m.p. 102°–104° C.

Preparation 8

Methyl-4-amino-1-methoxy naphthalene-2-carboxylate

Methyl-1-methoxy-4-nitro-naphthalene-2-carboxylate (2.6 g; 0.01 m) in ethanol (100 ml) was hydrogenated at 60 psi for 18 hours using 10% Pd/C as catalyst. The catalyst was removed by filtration and the solvent removed in vacuo to leave 2.3 g of pure methyl-4-amino-1-methoxy naphthalene-2-carboxylate.

Preparation 9

Methyl-4-dimethylamino-1-methoxy naphthalene-2-carboxylate

Sodium hydride (5 g, 5% dispersion in oil, 0.1 m) was added to dry THF (100 ml), followed by methyl 4-amino-1-methoxy naphthalene 2 carboxylate (3.0 g; 0.013 m). After stirring at room temperature for one hour, dimethyl sulphate (4.92 ml; 6.56 g; 0.052 m) was added in one portion and the solution refluxed overnight under nitrogen atmosphere. After cooling, the solution was slowly added to ice-water, followed by portionwise addition of sodium bicarbonate to neutral pH. Ethyl acetate (100 ml) was added and the organic layer separated. The aqueous layer was further extracted with ethyl acetate (2×50 ml), the organics collected and washed with water (3×100 ml) and dried over anhydrous magnesium sulphate. After filtration, the solvent was removed in vacuo. Flash chromatography of the resultant oil eluting with 5% methanol/dichloromethane gave the product methyl 4-dimethylamino-1-methoxy-naphthalene-2-carboxylate as a clear golden oil.

EXAMPLE 1

4-Bromo-N-[2-(cyclohexylamino)ethyl]-1-methoxy-naphthalene-2-carboxamide

To a solution of 4-bromo-1-methoxy-naphthalene-2-carboxylic acid (1.12 g; 0.004 m) in dry dichloromethane (60 ml) was added 1,1-carbonyl diimidazole (0.71 g; 0.0044 m) and the reaction stirred at room temperature for four hours. N-Cyclohexyl ethylene diamine (0.58 g; 0.004 m) was added and the reaction stirred at room temperature overnight. The solvent was removed in vacuo giving a solid which was dissolved in ethyl acetate (50 ml). This solution was washed with 2N sodium hydroxide (2×50 ml), with water (2×50 ml), dried, filtered and vacuumed to a solid, 4-bromo-N-[2-(cyclohexylamino)ethyl]-1-methoxy-naphthalene-2-carboxamide recrystallised from ethanol, m.p. 120°–122° C.

Similarly prepared were:

N-[2-(N-cyclohexylamino)ethyl]-1-methoxy-naphthalene-2-carboxamide HCl 176°–177° C.

N-[2-(cyclohexylamino)ethyl]-1,4-dimethoxy-naphthalene-2-carboxamide HCl 159°–160° C.

N-[2-(cycloheptylamino)ethyl]-1,4-dimethoxy-naphthalene-2-carboxamide HCl 137°–138° C.

N-[2-(cyclohexylamino)ethyl]-1,5-dimethoxy-naphthalene-2-carboxamide HCl 228°–230° C.

N-[2-(cyclohexylamino)ethyl]-4-dimethylamino-1-methoxy-naphthalene-2-carboxamide maleate 150°–152° C.

N-[2-(cycloheptylamino)ethyl]-4-dimethylamino-1-methoxy-naphthalene-2-carboxamide maleate 161°–162° C.

EXAMPLE 2

N-[2-(Cycloheptylamino)ethyl]-1-methoxy-4-methythio naphthalene-2-carboxamide maleate 1-Methoxy-4-methylthio naphthalene-2-carboxylic acid (430 mg; 1.73 mm) was dissolved in dichloromethane (30 ml) and oxalyl chloride (0.24 g; 1.9 mm) added, followed by dry dimethylformamide (2 drops). This solution was stirred at room temperature for one hour and then the solvent removed in vacuo. The residue was dissolved in dichloromethane (30 ml) and cycloheptyl ethylene diamine (0.27 g; 1.73 mm) added. This was stirred for a further hour when ammonia solution (5 ml) in water (50 ml) was added. Separation of the organic layer was followed by two further extractions with dichloromethane (2×50 ml). The organic fractions were collected, washed with water, dried, filtered and vacued to a solid. Flash chromatography was done eluting with 10% methanol/dichloromethane/1% ammonia to give N-[2-(cyclo-heptyl amino)ethyl]-1-methoxy-4-methylthio naphthalene-2-carboxamide which was recrystallised from ethyl acetate-ethanol as its maleate, m.p. 140°–141° C.

Similarly prepared were:

N-[2-(cycloheptylamino)ethyl]-1,3-dimethoxy-naphthalene-2-carboxamide hydrochloride, 165°–167° C.

N-[2-(cycloheptylamino)ethyl]-1,5-dimethoxy-naphthalene-2-carboxamide hydrochloride, 206°–208° C.

4-Chloro-N-[2-(cyclohexylamino)ethyl]-1-methoxy naphthalene-2-carboxamide hydrochloride, 206°–208° C.

4-Chloro-N-[2-(cycloheptylamino)ethyl]-1-methoxy naphthalene-2-carboxamide, HCl, 201°–203° C.

N-[2-(cyclohexylamino)ethyl]-1-methoxy-4-methylthio naphthalene-2-carboxamide maleate, 159°–160° C.

N-[2-(cyclohexylamino)ethyl]-1-methoxy-4-nitro naphthalene-2-carboxamide, HCl, 198°–200° C.

N-[2-cycloheptylamino)ethyl]-1-methoxy-4-nitro naphthalene-2-carboxamide, HCl, 205°–207° C.

EXAMPLE 3

4-Amino-N-[2-(cyclohexylamino)ethyl]-1-methoxy naphthalene-2-carboxamide, HCl A solution of N-[2-(cyclohexylamino)ethyl]-1-methoxy-4-nitro naphthalene-2-carboxamide hydrochloride (0.38 g, 0.001 m) in ethanol (100 ml) was hydrogenated at 60 psi using 5% Pd/C as catalyst for 18 hours. The catalyst was removed by filtration and the solvent removed in vacuo. The product was crystallised from ethanol/ether to give 0.3 g of 4-amino-N-[2-(cyclohexylamino)ethyl]-1-methoxy naphthalene-2-carboxamide hydrochloride, m.p. 250°–252° C.

Similarly prepared was 4-amino-N-[2-(cycloheptylamine)ethyl]-1-methoxy naphthalene-2-carboxamide, hydrochloride, m.p. 220°–222° C.

EXAMPLE 4

Tablets each containing 10 mg of active ingredient are made up as follows:

| | |
|---|---|
| Active ingredient | 10 mg |
| Starch | 160 mg |
| Microcrystalline cellulose | 100 mg |
| Polyvinylpyrrolidone (as 10% solution in water) | 13 mg |
| Sodium carboxymethyl starch | 14 mg |
| Magnesium stearate | 3 mg |

-continued

| | |
|---|---|
| Total | 300 mg |

The active ingredient, starch and cellulose are mixed thoroughly. The solution of polyvinylpyrrolidone is mixed with the resultant powders and passed through a sieve. The granules so produced are dried and re-passed through a sieve. The sodium carboxymethyl starch and magnesium stearate are then added to the granules which, after mixing, are compressed on a tablet machine to yield tablets each weighing 300 mg.

EXAMPLE 5

Capsules each containing 20 mg of medicament are made as follows:

| | |
|---|---|
| Active ingredient | 20 mg |
| Dried starch | 178 mg |
| Magnesium stearate | 2 mg |
| Total | 200 mg |

The active ingredient, starch and magnesium stearate are passed through a sieve and filled into hard gelatin capsules in 200 mg quantities.

EXAMPLE 6

A freeze dried formulation for reconstitution into an aqueous injection is prepared from the following ingredients:

| | |
|---|---|
| Active ingredient | 15 mg |
| 0.1M Hydrochloric acid | 0.48 ml |
| Mannitol | 100 mg |
| Water | to 2 ml |

The active ingredient is suspended in water, acidified with hydrochloric acid and mannitol added, and adjusted to pH5. Water is added to 2 ml and the mixture filled into vials and then freeze dried.

EXAMPLE 7

A sustained release formulation for intramuscular injection is prepared from the following ingredients:

| | |
|---|---|
| Active ingredient | 20 mg |
| Aluminium stearate | 2 mg |
| Soya bean oil | to 2 ml |

We claim:
1. A compound of the formula:

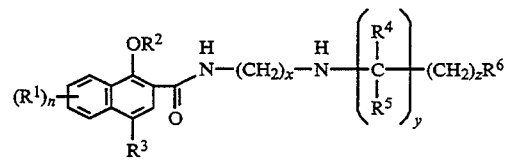

in which $R^1$ is hydrogen, $C_{1-4}$ alkyl, $C_{1-4}$ alkoxy, halogen or nitro, and n is 0, 1, 2, or 3, $R^2$ is hydrogen, $C_{1-4}$ alkyl or $C_{2-4}$ alkenyl, $R^3$ is hydrogen, $C_{1-4}$ alkyl, $C_{1-4}$ alkoxy, $C_{1-4}$ alkylthio, halogen, nitro or —NR'R'' where R' and R'' are each hydrogen or $C_{1-4}$ alkyl, $R^4$ and $R^5$ are each hydrogen, $C_{1-4}$ alkyl, optionally substituted phenyl or $C_{6-9}$ cycloalkyl optionally substituted by 1 to 4 $C_{1-4}$ alkyl groups, $R^6$ is $C_{6-10}$ cycloalkyl optionally substituted with 1 to 4 $C_{1-4}$ alkyl groups or a phenyl group, or $C_{4-9}$ heterosubstituted cycloalkyl optionally substituted with 1–4 alkyl groups, x is 1, 2 or 3, y is 0 or 1 and z is 0, 1, 2 or 3; or a salt thereof.

2. A compound according to claim 1, in which n is 0 and $R^2$ is $C_{1-4}$ alkyl.

3. A compound according to claim 2, in which $R^3$ is $C_{1-4}$ alkoxy, $C_{1-4}$ alkylthio, halogen, nitro, —$NH_2$ or —N$(CH_3)_2$.

4. A compound according to claim 1 in which n is 0, $R^2$ is $C_{1-4}$ alkyl, $R^3$ is $C_{1-4}$ alkoxy, $C_{1-4}$ alkylthio, halogen, nitro, —$NH_2$ or —N$(CH_3)_2$, x is 2, y is 0, z is 0, 1 or 2 and $R^6$ is $C_{6-9}$ cyclalkyl.

5. A compound according to claim 1 in which n is 0, $R^2$ is $C_{1-4}$ alkyl, $R^3$ is $C_{1-4}$ alkoxy, $C_{1-4}$ alkylthio, halogen, nitro, —$NH_2$ or —N $(CH_3)_2$, x is 2, y is 1, z is 0, $R^4$ is hydrogen, and $R^5$ and $R^6$ are each $C_{6-9}$ cycloalkyl.

6. A pharmaceutical formulation comprising a compound according to claim 1 or a pharmaceutically acceptable salt thereof together with a pharmaceutically-acceptable diluent or carrier therefor.

7. A method for treating a mammal suffering from or susceptible to which comprises administering an effective amount of a compound according to claim 1, or a pharmaceutically acceptable salt thereof.

* * * * *